(12) United States Patent
Stack et al.

(10) Patent No.: US 8,029,455 B2
(45) Date of Patent: Oct. 4, 2011

(54) SATIATION POUCHES AND METHODS OF USE

(75) Inventors: Richard S. Stack, Chapel Hill, NC (US); William L. Athas, Durham, NC (US); Richard A. Glenn, Chapel Hill, NC (US); Dan Balbierz, Redwood City, CA (US); John Lunsford, San Carlos, CA (US); Michael S. Williams, Santa Rosa, CA (US)

(73) Assignee: Barosense, Inc., Redwood City, CA (US)

( * ) Notice: Subject to any disclaimer, the term of this patent is extended or adjusted under 35 U.S.C. 154(b) by 0 days.

(21) Appl. No.: 12/398,917

(22) Filed: Mar. 5, 2009

(65) Prior Publication Data

US 2009/0177215 A1 Jul. 9, 2009

Related U.S. Application Data

(62) Division of application No. 10/345,666, filed on Jan. 16, 2003, now abandoned.

(51) Int. Cl.
*A61M 5/00* (2006.01)

(52) U.S. Cl. ......................................... 604/8; 623/23.65

(58) Field of Classification Search .... 623/23.64–23.68, 623/23.7, 1.24, 1.26, 1.15; 604/8
See application file for complete search history.

(56) References Cited

U.S. PATENT DOCUMENTS

| | | | |
|---|---|---|---|
| 1,408,865 A | 3/1922 | Cowell | |
| 3,663,965 A | 5/1972 | Lee et al. | |
| 4,134,405 A | 1/1979 | Smit | |
| 4,207,890 A | 6/1980 | Mamajek et al. | |
| 4,246,893 A | 1/1981 | Berson | |
| 4,315,509 A | 2/1982 | Smit | |
| 4,331,277 A | 5/1982 | Green | |
| 4,403,604 A | 9/1983 | Wilkinson et al. | |
| 4,416,267 A | 11/1983 | Garren et al. | |
| 4,417,360 A | 11/1983 | Moasser | |
| 4,441,215 A | 4/1984 | Kaster | |
| 4,467,804 A | 8/1984 | Hardy et al. | |
| 4,485,805 A | 12/1984 | Foster, Jr. | |
| 4,501,264 A | 2/1985 | Rockey | |
| 4,607,618 A | 8/1986 | Angelchik | |

(Continued)

FOREIGN PATENT DOCUMENTS

CH 680263 A5 7/1992

(Continued)

OTHER PUBLICATIONS

International Search Report from PCT Patent Application No. PCT/US2002/027177 mailed Feb. 14, 2003.

(Continued)

*Primary Examiner* — Alvin J Stewart
(74) *Attorney, Agent, or Firm* — King & Spalding LLP; Peter J. Dehlinger; Kathleen A. Frost

(57) ABSTRACT

A method for controlling appetite by means of a satiation device is disclosed. The device, which includes a flexible webbing defining proximal and distal openings and a biasing structure, is attached to the patient's stomach with the proximal opening positioned adjacent and below the patient's gastro-esophageal junction. The biasing structure imparts pressure against the wall of the patient's stomach adjacent the gastro-esophageal junction.

8 Claims, 9 Drawing Sheets

U.S. PATENT DOCUMENTS

| | | | |
|---|---|---|---|
| 4,617,932 A * | 10/1986 | Kornberg | 606/108 |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,747,849 A | 5/1988 | Galitier | |
| 4,846,836 A | 7/1989 | Reich | |
| 4,848,367 A | 7/1989 | Avant et al. | |
| 4,899,747 A | 2/1990 | Garren et al. | |
| 4,925,446 A | 5/1990 | Garay et al. | |
| 4,946,440 A | 8/1990 | Hall | |
| 4,969,896 A | 11/1990 | Shors | |
| 4,997,084 A | 3/1991 | Opie et al. | |
| 5,006,106 A | 4/1991 | Angelchik | |
| 5,037,021 A | 8/1991 | Mills et al. | |
| 5,061,275 A | 10/1991 | Wallsten et al. | |
| 5,084,061 A | 1/1992 | Gau et al. | |
| 5,088,979 A | 2/1992 | Filipi et al. | |
| 5,163,952 A | 11/1992 | Froix | |
| 5,211,658 A | 5/1993 | Clouse | |
| 5,234,454 A | 8/1993 | Bangs | |
| 5,246,456 A | 9/1993 | Wilkinson | |
| 5,259,399 A | 11/1993 | Brown | |
| 5,263,629 A | 11/1993 | Trumbull et al. | |
| 5,290,217 A | 3/1994 | Campos | |
| 5,306,300 A * | 4/1994 | Berry | 623/23.64 |
| 5,314,473 A | 5/1994 | Godin | |
| 5,327,914 A | 7/1994 | Shlain | |
| 5,345,949 A | 9/1994 | Shain | |
| 5,355,897 A | 10/1994 | Pietrafitta et al. | |
| 5,401,241 A | 3/1995 | Delany | |
| 5,403,326 A | 4/1995 | Harrison et al. | |
| 5,405,377 A | 4/1995 | Cragg | |
| 5,431,673 A | 7/1995 | Summers et al. | |
| 5,486,187 A | 1/1996 | Schenck | |
| 5,514,176 A | 5/1996 | Bosley, Jr. | |
| 5,535,935 A | 7/1996 | Vidal et al. | |
| 5,542,949 A | 8/1996 | Yoon | |
| 5,562,239 A | 10/1996 | Boiarski et al. | |
| 5,571,116 A | 11/1996 | Bolanos et al. | |
| 5,577,654 A | 11/1996 | Bishop | |
| 5,593,434 A | 1/1997 | Williams | |
| 5,597,107 A | 1/1997 | Knodel et al. | |
| 5,609,624 A | 3/1997 | Kalis | |
| 5,628,786 A | 5/1997 | Banas et al. | |
| 5,630,539 A | 5/1997 | Plyley et al. | |
| 5,647,526 A | 7/1997 | Green et al. | |
| 5,653,743 A | 8/1997 | Martin | |
| 5,662,713 A * | 9/1997 | Andersen et al. | 128/898 |
| 5,673,841 A | 10/1997 | Schulze et al. | |
| 5,674,241 A | 10/1997 | Bley et al. | |
| 5,706,998 A | 1/1998 | Plyley et al. | |
| 5,709,657 A | 1/1998 | Zimmon | |
| 5,720,776 A * | 2/1998 | Chuter et al. | 623/1.36 |
| 5,749,918 A | 5/1998 | Hogendijk et al. | |
| 5,762,255 A | 6/1998 | Chrisman et al. | |
| 5,771,903 A | 6/1998 | Jakobsson | |
| 5,785,684 A | 7/1998 | Zimmon | |
| 5,792,119 A | 8/1998 | Marx | |
| 5,820,584 A * | 10/1998 | Crabb | 604/500 |
| 5,839,639 A | 11/1998 | Sauer et al. | |
| 5,848,964 A | 12/1998 | Samuels | |
| 5,855,311 A | 1/1999 | Hamblin et al. | |
| 5,855,601 A | 1/1999 | Bessler et al. | |
| 5,856,445 A | 1/1999 | Korsmeyer | |
| 5,861,036 A | 1/1999 | Godin | |
| 5,868,141 A | 2/1999 | Ellias | |
| 5,887,594 A | 3/1999 | LoCicero, III | |
| 5,897,562 A | 4/1999 | Bolanos et al. | |
| 5,910,144 A | 6/1999 | Hayashi et al. | |
| 5,922,019 A | 7/1999 | Hankh et al. | |
| 5,947,983 A | 9/1999 | Solar et al. | |
| 5,993,473 A | 11/1999 | Chan et al. | |
| 5,993,483 A | 11/1999 | Gianotti | |
| 6,016,848 A | 1/2000 | Egres, Jr. | |
| 6,051,015 A | 4/2000 | Maahs | |
| 6,086,600 A | 7/2000 | Kortenbach | |
| 6,098,629 A | 8/2000 | Johnson et al. | |
| 6,102,922 A | 8/2000 | Jakobsson et al. | |
| 6,113,609 A | 9/2000 | Adams | |
| 6,120,534 A | 9/2000 | Ruiz | |
| 6,146,416 A | 11/2000 | Andersen et al. | |
| 6,159,146 A | 12/2000 | El Gazayerli | |
| 6,159,238 A | 12/2000 | Killion et al. | |
| 6,197,022 B1 | 3/2001 | Baker | |
| 6,206,930 B1 | 3/2001 | Burg et al. | |
| 6,245,088 B1 | 6/2001 | Lowery | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,287,334 B1 | 9/2001 | Moll et al. | |
| 6,302,917 B1 | 10/2001 | Dua et al. | |
| 6,358,197 B1 | 3/2002 | Silverman et al. | |
| 6,416,522 B1 | 7/2002 | Strecker | |
| 6,425,916 B1 | 7/2002 | Garrison et al. | |
| 6,454,785 B2 | 9/2002 | De Hoyos Garza | |
| 6,460,543 B1 | 10/2002 | Forsell | |
| 6,461,366 B1 | 10/2002 | Seguin | |
| 6,494,888 B1 | 12/2002 | Laufer et al. | |
| 6,494,895 B2 | 12/2002 | Addis | |
| 6,503,264 B1 | 1/2003 | Birk | |
| 6,506,196 B1 | 1/2003 | Laufer et al. | |
| 6,527,784 B2 | 3/2003 | Adams et al. | |
| 6,540,789 B1 | 4/2003 | Silverman et al. | |
| 6,544,291 B2 | 4/2003 | Taylor | |
| 6,547,801 B1 | 4/2003 | Dargent et al. | |
| 6,558,400 B2 | 5/2003 | Deem et al. | |
| 6,558,429 B2 | 5/2003 | Taylor | |
| 6,572,627 B2 | 6/2003 | Gabbay | |
| 6,572,629 B2 | 6/2003 | Kalloo | |
| 6,575,896 B2 | 6/2003 | Silverman | |
| 6,592,596 B1 | 7/2003 | Geitz et al. | |
| 6,596,023 B1 | 7/2003 | Nunez et al. | |
| 6,607,555 B2 | 8/2003 | Patterson et al. | |
| 6,627,206 B2 | 9/2003 | Lloyd | |
| 6,632,227 B2 | 10/2003 | Adams | |
| 6,663,639 B1 | 12/2003 | Laufer et al. | |
| 6,675,809 B2 * | 1/2004 | Stack et al. | 128/898 |
| 6,740,098 B2 | 5/2004 | Abrams et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,764,518 B2 | 7/2004 | Godin | |
| 6,773,440 B2 | 8/2004 | Gannoe et al. | |
| 6,773,441 B1 | 8/2004 | Laufer et al. | |
| 6,790,214 B2 | 9/2004 | Kraemer et al. | |
| 6,790,237 B2 | 9/2004 | Stinson | |
| 6,821,285 B2 | 11/2004 | Laufer et al. | |
| 6,835,200 B2 | 12/2004 | Laufer et al. | |
| 6,845,776 B2 | 1/2005 | Stack et al. | |
| 6,916,332 B2 | 7/2005 | Adams | |
| 6,932,838 B2 | 8/2005 | Schwartz et al. | |
| 6,960,233 B1 | 11/2005 | Berg et al. | |
| 6,966,875 B1 | 11/2005 | Longobardi | |
| 6,981,978 B2 | 1/2006 | Gannoe | |
| 6,981,980 B2 | 1/2006 | Sampson et al. | |
| 6,994,715 B2 | 2/2006 | Gannoe et al. | |
| 7,011,094 B2 | 3/2006 | Rapackie et al. | |
| 7,020,531 B1 | 3/2006 | Colliou et al. | |
| 7,025,791 B2 * | 4/2006 | Levine et al. | 623/23.64 |
| 7,033,373 B2 | 4/2006 | de la Torre et al. | |
| 7,033,384 B2 | 4/2006 | Gannoe et al. | |
| 7,037,344 B2 * | 5/2006 | Kagan et al. | 623/23.65 |
| 7,056,305 B2 | 6/2006 | Garza Alvarez | |
| 7,066,945 B2 | 6/2006 | Hashiba et al. | |
| 7,083,629 B2 | 8/2006 | Weller et al. | |
| 7,090,699 B2 | 8/2006 | Geitz | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,112,186 B2 | 9/2006 | Shah | |
| 7,120,498 B2 | 10/2006 | Imran et al. | |
| 7,121,283 B2 | 10/2006 | Stack et al. | |
| 7,146,984 B2 | 12/2006 | Stack et al. | |
| 7,147,140 B2 | 12/2006 | Wukusick et al. | |
| 7,152,607 B2 | 12/2006 | Stack et al. | |

| | | | | | |
|---|---|---|---|---|---|
| 7,160,312 B2 | 1/2007 | Saadat et al. | 2004/0162568 A1 | 8/2004 | Saadat et al. |
| 7,172,613 B2 | 2/2007 | Wazne | 2004/0172141 A1 | 9/2004 | Stack et al. |
| 7,175,638 B2 | 2/2007 | Gannoe et al. | 2004/0172142 A1 | 9/2004 | Stack et al. |
| 7,175,660 B2 | 2/2007 | Cartledge et al. | 2004/0186502 A1 | 9/2004 | Sampson et al. |
| 7,211,114 B2 * | 5/2007 | Bessler et al. ............ 623/23.65 | 2004/0210243 A1 | 10/2004 | Gannoe et al. |
| 7,214,233 B2 | 5/2007 | Gannoe et al. | 2004/0215216 A1 | 10/2004 | Gannoe et al. |
| 7,220,237 B2 | 5/2007 | Gannoe et al. | 2004/0220682 A1 | 11/2004 | Levine et al. |
| 7,220,284 B2 | 5/2007 | Kagan et al. | 2004/0225183 A1 | 11/2004 | Michlitsch et al. |
| 7,223,277 B2 | 5/2007 | DeLegge | 2004/0225305 A1 | 11/2004 | Ewers et al. |
| 7,229,428 B2 * | 6/2007 | Gannoe et al. .................... 604/8 | 2004/0236419 A1 | 11/2004 | Milo |
| 7,229,453 B2 | 6/2007 | Anderson et al. | 2004/0243152 A1 | 12/2004 | Taylor et al. |
| 7,255,675 B2 | 8/2007 | Gertner et al. | 2004/0243223 A1 | 12/2004 | Kraemer et al. |
| 7,261,722 B2 | 8/2007 | McGuckin, Jr. et al. | 2004/0267378 A1 | 12/2004 | Gazi et al. |
| 7,288,101 B2 | 10/2007 | Deem et al. | 2005/0004430 A1 | 1/2005 | Lee et al. |
| 7,306,614 B2 | 12/2007 | Weller et al. | 2005/0004681 A1 | 1/2005 | Stack et al. |
| 7,315,509 B2 | 1/2008 | Jeong et al. | 2005/0033326 A1 | 2/2005 | Briganti et al. |
| 7,316,716 B2 * | 1/2008 | Egan ........................ 623/23.65 | 2005/0033345 A1 | 2/2005 | DeLegge |
| 7,320,696 B2 | 1/2008 | Gazi et al. | 2005/0049718 A1 | 3/2005 | Dann et al. |
| 7,326,207 B2 | 2/2008 | Edwards | 2005/0075654 A1 | 4/2005 | Kelleher |
| 7,335,210 B2 | 2/2008 | Smit | 2005/0080444 A1 | 4/2005 | Kraemer et al. |
| 7,347,863 B2 | 3/2008 | Rothe et al. | 2005/0085787 A1 | 4/2005 | Laufer et al. |
| 7,347,875 B2 | 3/2008 | Levine et al. | 2005/0096673 A1 | 5/2005 | Stack et al. |
| 7,354,454 B2 | 4/2008 | Stack et al. | 2005/0096750 A1 | 5/2005 | Kagan et al. |
| 7,399,304 B2 | 7/2008 | Gambale et al. | 2005/0149114 A1 | 7/2005 | Cartledge et al. |
| 7,431,725 B2 | 10/2008 | Stack et al. | 2005/0159769 A1 | 7/2005 | Alverdy |
| 7,461,767 B2 | 12/2008 | Viola et al. | 2005/0177181 A1 | 8/2005 | Kagan et al. |
| 7,470,251 B2 | 12/2008 | Shah | 2005/0183732 A1 | 8/2005 | Edwards |
| 7,485,142 B2 | 2/2009 | Milo | 2005/0192599 A1 | 9/2005 | Demarais |
| 7,615,064 B2 | 11/2009 | Bjerken | 2005/0192615 A1 | 9/2005 | Torre et al. |
| 7,753,870 B2 * | 7/2010 | Demarais et al. ................ 604/8 | 2005/0216040 A1 | 9/2005 | Gertner et al. |
| 7,766,861 B2 * | 8/2010 | Levine et al. ................... 604/57 | 2005/0216042 A1 | 9/2005 | Gertner |
| 7,846,138 B2 | 12/2010 | Dann et al. | 2005/0240279 A1 | 10/2005 | Kagan et al. |
| 7,846,174 B2 | 12/2010 | Baker et al. | 2005/0247320 A1 | 11/2005 | Stack et al. |
| 2001/0011543 A1 | 8/2001 | Forsell | 2005/0250803 A1 | 11/2005 | Swanstrom et al. |
| 2001/0020189 A1 | 9/2001 | Taylor | 2005/0251158 A1 | 11/2005 | Saadat et al. |
| 2001/0020190 A1 | 9/2001 | Taylor | 2005/0251162 A1 | 11/2005 | Rothe et al. |
| 2001/0021796 A1 | 9/2001 | Silverman et al. | 2005/0256533 A1 | 11/2005 | Roth et al. |
| 2001/0044595 A1 | 11/2001 | Reydel et al. | 2005/0256587 A1 | 11/2005 | Egan |
| 2002/0022851 A1 | 2/2002 | Kalloo et al. | 2005/0261712 A1 | 11/2005 | Balbierz et al. |
| 2002/0055757 A1 | 5/2002 | Torre et al. | 2005/0267405 A1 | 12/2005 | Shah |
| 2002/0072761 A1 | 6/2002 | Abrams et al. | 2005/0267499 A1 | 12/2005 | Stack et al. |
| 2002/0082621 A1 | 6/2002 | Schurr et al. | 2005/0267595 A1 | 12/2005 | Chen et al. |
| 2002/0099439 A1 | 7/2002 | Schwartz et al. | 2005/0267596 A1 | 12/2005 | Chen et al. |
| 2002/0183767 A1 | 12/2002 | Adams et al. | 2005/0273060 A1 | 12/2005 | Levy et al. |
| 2002/0183768 A1 | 12/2002 | Deem et al. | 2006/0015006 A1 | 1/2006 | Laurence et al. |
| 2003/0009236 A1 | 1/2003 | Godin | 2006/0020278 A1 | 1/2006 | Burnette et al. |
| 2003/0040804 A1 | 2/2003 | Stack et al. | 2006/0058829 A1 | 3/2006 | Sampson et al. |
| 2003/0040808 A1 | 2/2003 | Stack et al. | 2006/0129094 A1 | 6/2006 | Shah |
| 2003/0065359 A1 | 4/2003 | Weller et al. | 2006/0151568 A1 | 7/2006 | Weller et al. |
| 2003/0093117 A1 | 5/2003 | Saadat et al. | 2006/0155259 A1 | 7/2006 | MacLay |
| 2003/0109892 A1 | 6/2003 | Deem et al. | 2006/0155311 A1 | 7/2006 | Hashiba et al. |
| 2003/0120289 A1 | 6/2003 | McGuckin, Jr. et al. | 2006/0178560 A1 | 8/2006 | Saadat et al. |
| 2003/0158569 A1 | 8/2003 | Wazne | 2006/0178691 A1 | 8/2006 | Binmoeller |
| 2003/0191476 A1 | 10/2003 | Smit | 2006/0195139 A1 | 8/2006 | Gertner |
| 2003/0199989 A1 | 10/2003 | Stack et al. | 2006/0253142 A1 | 11/2006 | Bjerken |
| 2003/0199990 A1 | 10/2003 | Stack et al. | 2006/0271076 A1 | 11/2006 | Weller et al. |
| 2003/0199991 A1 | 10/2003 | Stack et al. | 2006/0282095 A1 | 12/2006 | Stokes et al. |
| 2003/0208209 A1 | 11/2003 | Gambale et al. | 2006/0287734 A1 | 12/2006 | Stack et al. |
| 2003/0220660 A1 | 11/2003 | Kortenbach et al. | 2007/0010864 A1 | 1/2007 | Dann et al. |
| 2004/0006351 A1 | 1/2004 | Gannoe et al. | 2007/0032800 A1 | 2/2007 | Ortiz et al. |
| 2004/0024386 A1 | 2/2004 | Deem et al. | 2007/0043384 A1 | 2/2007 | Ortiz et al. |
| 2004/0030347 A1 | 2/2004 | Gannoe et al. | 2007/0055292 A1 | 3/2007 | Ortiz et al. |
| 2004/0044353 A1 | 3/2004 | Gannoe | 2007/0060932 A1 | 3/2007 | Stack et al. |
| 2004/0044354 A1 | 3/2004 | Gannoe et al. | 2007/0149994 A1 | 6/2007 | Sosnowski et al. |
| 2004/0044357 A1 | 3/2004 | Gannoe et al. | 2007/0175488 A1 | 8/2007 | Cox et al. |
| 2004/0044364 A1 | 3/2004 | DeVries et al. | 2007/0191870 A1 | 8/2007 | Baker et al. |
| 2004/0082963 A1 | 4/2004 | Gannoe et al. | 2007/0191871 A1 | 8/2007 | Baker et al. |
| 2004/0088023 A1 | 5/2004 | Imran et al. | 2007/0198074 A1 | 8/2007 | Dann et al. |
| 2004/0092892 A1 | 5/2004 | Kagan et al. | 2007/0219571 A1 | 9/2007 | Balbierz et al. |
| 2004/0092974 A1 | 5/2004 | Gannoe et al. | 2007/0239284 A1 | 10/2007 | Skerven et al. |
| 2004/0093091 A1 | 5/2004 | Gannoe et al. | 2007/0260327 A1 | 11/2007 | Case et al. |
| 2004/0098043 A1 | 5/2004 | Trout | 2007/0276432 A1 | 11/2007 | Stack et al. |
| 2004/0107004 A1 | 6/2004 | Levine et al. | 2008/0033574 A1 | 2/2008 | Bessler et al. |
| 2004/0117031 A1 | 6/2004 | Stack et al. | 2008/0065122 A1 | 3/2008 | Stack et al. |
| 2004/0138761 A1 | 7/2004 | Stack et al. | 2008/0116244 A1 | 5/2008 | Rethy et al. |
| 2004/0143342 A1 | 7/2004 | Stack et al. | 2008/0190989 A1 | 8/2008 | Crews et al. |
| 2004/0148034 A1 | 7/2004 | Kagan et al. | 2008/0195226 A1 | 8/2008 | Williams et al. |
| 2004/0153167 A1 | 8/2004 | Stack et al. | 2008/0208355 A1 | 8/2008 | Stack et al. |
| 2004/0158331 A1 | 8/2004 | Stack et al. | 2008/0208356 A1 | 8/2008 | Stack et al. |

| | | | |
|---|---|---|---|
| 2008/0269797 | A1 | 10/2008 | Stack et al. |
| 2008/0294179 | A1 | 11/2008 | Balbierz et al. |
| 2009/0018558 | A1 | 1/2009 | Laufer et al. |
| 2009/0024143 | A1 | 1/2009 | Crews et al. |
| 2009/0030284 | A1 | 1/2009 | Cole et al. |

FOREIGN PATENT DOCUMENTS

| | | |
|---|---|---|
| EP | 0 775 471 B1 | 5/1997 |
| EP | 1492478 | 1/2005 |
| EP | 1602336 | 12/2005 |
| FR | 2768324 | 3/1999 |
| JP | 09-168597 | 6/1997 |
| WO | WO 91/01117 A1 | 2/1991 |
| WO | WO 97/47231 | 12/1997 |
| WO | WO 00/12027 A1 | 3/2000 |
| WO | WO 00/32137 A1 | 6/2000 |
| WO | WO 00/78227 | 12/2000 |
| WO | WO 01/41671 | 6/2001 |
| WO | WO 01/45485 | 6/2001 |
| WO | WO 01/49359 A1 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 A1 | 11/2003 |
| WO | WO 03/099137 | 12/2003 |
| WO | WO 2004/019765 | 3/2004 |
| WO | WO 2004/019787 | 3/2004 |
| WO | WO 2004/032760 | 4/2004 |
| WO | WO 2004/037064 | 5/2004 |
| WO | WO 2004/041133 A1 | 5/2004 |
| WO | WO 2004/064680 | 8/2004 |
| WO | WO 2004/064685 | 8/2004 |
| WO | WO 2004/080336 | 9/2004 |
| WO | WO 2004/110285 | 12/2004 |
| WO | WO 2005/037152 | 4/2005 |
| WO | WO 2005/079673 | 9/2005 |
| WO | WO 2005/096991 | 10/2005 |
| WO | WO 2005/105003 | 11/2005 |
| WO | WO 2006/016894 | 2/2006 |
| WO | WO 2006/055365 | 5/2006 |
| WO | WO 2006/127593 | 11/2006 |
| WO | WO 2007/041598 | 4/2007 |
| WO | WO 2008/030403 | 3/2008 |
| WO | WO 2008/033409 | 3/2008 |
| WO | WO 2008/033474 | 3/2008 |
| WO | WO 2008/141288 | 11/2008 |
| WO | WO 2009/001182 | 1/2009 |
| WO | WO 2009/011881 | 1/2009 |
| WO | WO 2009/086549 | 7/2009 |

OTHER PUBLICATIONS

International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2004/033007 mailed Feb. 9, 2005.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
International Search Report from PCT Patent Application No. PCT/US2007/019833 mailed Feb. 20, 2008.
International Search Report from PCT Patent Application No. PCT/US2007/019940 mailed Mar. 14, 2008.
International Search Report from PCT Patent Application No. PCT/US2008/008726 mailed Oct. 16, 2008.
International Search Report from PCT Patent Application No. PCT/US2008/008729 mailed Aug. 18, 2009.
International Search Report from PCT Patent Application No. PCT/US2008/063440 mailed Aug. 1, 2008.
International Search Report from PCT Patent Application No. PCT/US2008/088581 mailed Feb. 26, 2009.
Felsher, et al., "Mucosal apposition in endoscopic suturing", Gastrointestinal Endoscopy, vol. 58, No. 6, pp. 867-870, (2003).
Stecco, et al., "Trans-oral plication formation and gastric implant placement in a canine model", Stecco Group, San Jose and Barosense, Inc., Redwood City, CA (2004).
Stecco, et al. "Safety of a gastric restrictive implant in a canine model", Stecco group, San Jose amd Barosense, Inc., Redwood City, CA (2004).

* cited by examiner

SATIATION POUCHES AND METHODS OF USE

This patent application is a divisional of U.S. patent application Ser. No. 10/345,666 filed on Jan. 16, 2003 now abandoned, which is incorporated in its entirety herein by reference.

FIELD OF THE INVENTION

The present invention relates generally to the field of devices and methods for achieving weight loss in humans, and specifically to the use of devices implantable within the human stomach for controlling feelings of hunger and/or limiting food intake.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Prosthetic devices for use in controlling obesity are shown and described in U.S. application Ser. No. 09/940,110, filed Aug. 27, 2001 and U.S. application Ser. No. 10/118,289 filed Apr. 8, 2002, and U.S. Provisional Application No. 60/379,306 filed May 10, 2002. These applications are owned by the assignee of the present application, and the disclosures of these applications are incorporated herein by reference. Certain forms of these devices involve positioning a prosthetic pouch in the proximal stomach as shown in FIG. 1B. The pouch 2 includes a proximal opening 4 and a smaller distal opening 6 and forms a small reservoir that collects masticated food from the esophagus—thereby limiting the amount of food that can be consumed at one time. As the pouch fills with food, it may distend, imparting pressure against the upper stomach and lower esophageal sphincter causing the patient to experience sensations of fullness. The pouch may additionally or alternatively act as a restrictor, limiting the amount of food intake. The pouch is fixed in place using clips, sutures, suitable adhesives or other means 8 at anchor points around the perimeter of the proximal opening 4.

Because of the flexible nature of the tissue of the gastro-esophageal junction region and/or the material forming the pouch, gaps 9 can occur along the perimeter of the pouch in regions between neighboring anchor points. Solving this problem is made more difficult by the flared geometry of the walls of the proximal stomach. Food entering or accumulating in the pouch 2 can ooze from these gaps and pass around the exterior of the pouch directly into the stomach, thereby decreasing the effectiveness of the prosthesis. The embodiments described herein optimize the function of the pouch devices by forming a barrier against passage of food through any such gaps and/or by eliminating such gaps.

SUMMARY OF THE INVENTION

The present invention includes a prosthetic device positionable within the gastro-esophageal junction region of a patient, wherein the prosthetic device includes a proximal opening and a barrier device defining a central passage at least partially aligned with the proximal opening of the prosthetic device. In a method for positioning the prosthetic device, the prosthetic device is attached to tissue of the gastro-esophageal region of the patient, with the device positioned such that food ingested by the patient passes from the esophagus through the central passage and proximal opening into the interior of the prosthetic device. The barrier contacts surrounding tissue and thereby minimizes passage of food from the esophagus around the exterior of the prosthetic device. In preferred forms of the embodiment, the barrier is adaptable in response to movement of the surrounding tissue to maintain contact between the barrier and the surrounding tissue.

DETAILED DESCRIPTION OF THE DRAWINGS

Figure 1A:
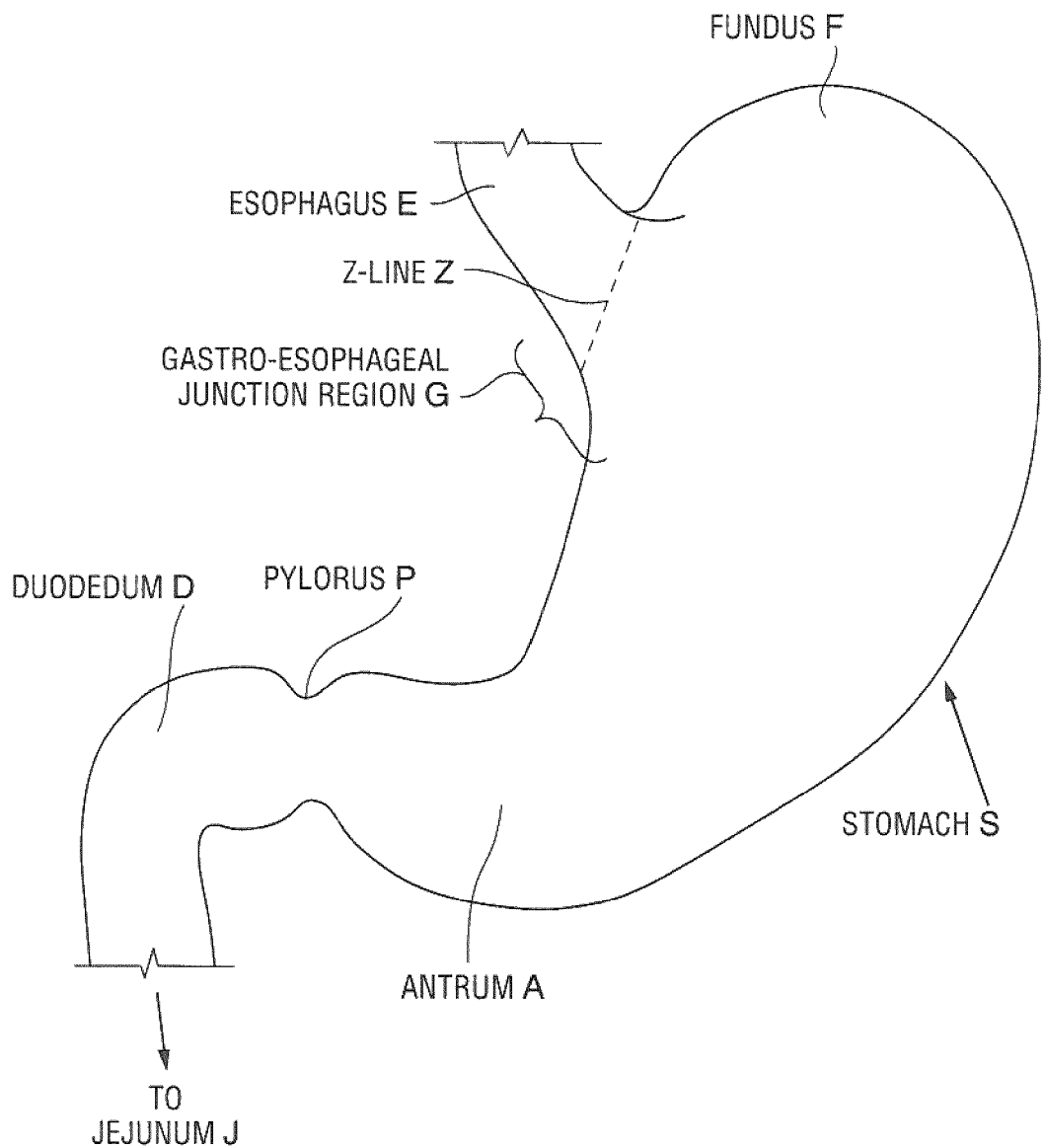
FIG. 1A is a schematic illustration of a human stomach and a portion of the small intestine.

The drawings show a number of embodiments of satiation pouches having features that create a barrier against passage of food through gaps occurring between the upper perimeter of the pouch and adjacent tissue and/or that minimize or eliminate such gaps. Ideally, the barriers will form a seal with the adjacent tissue, however it is sufficient that the barriers prevent a substantial amount of food from passing between the exterior of the pouch and adjacent tissue, without necessarily forming an impermeable seal.

For the purposes of this application, the term "satiation devices" or "satiation pouches" will be used to mean devices or pouches intended to induce weight loss in one or more of a variety of ways. These include, but are not limited to, physically restricting the amount of food that can be consumed, and/or imparting pressure against portions of the body (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body.

The pouch of each described embodiment may be formed of a flexible material that will prevent passage of food through the sides of the pouch. Examples of such materials include, but are not limited to polyesters (e.g. Dacron® polyester), ePTFE fabric (e.g. GoreTex® fabric or others), a polyurethane such as ChronoFlex® polyurethane, nylon fabrics, silicone, other polymeric materials, and bio-absorbable materials (e.g. PLLA, PGA, PCL, poly-amhydride etc). The material may be a composite of compliant, semi-compliant and/or non-compliant materials that give different regions of the pouch different degrees of compliance so as to allow/limit expansion of the pouch in various locations. For example, it may be desirable to provide the pouch with a fairly elastic exit port to as to prevent occlusion in the event a large piece of food is ingested and/or to control the exit pressure of food from the pouch, whereas the proximal end of the pouch may be stiffer to prevent bulging. Varying degrees of compliance may also be built into the pouch by varying the cross-sectional thickness in different regions of the pouch. The material may be coated with a lubricious, bio-compatible, chemically inert material, such as paraleyne, to reduce friction on the base material's surface which will help prevent sticking and food build up on the device. The flexible pouch material may be reinforced with, constructed of, or supported by supporting members, such as a soft mesh, a cage structure, ribs, rings etc. The supporting members may be formed of stainless steel, polymer, shape memory materials such as nitinol, shape memory alloys, or shape memory polymers, or thickened regions of material. The pouch may be constructed so as to be self-expanding, such that the pouch springs radially open into an expanded condition upon ejection from a deployment device or catheter.

Implantation of the described devices is preferably performed endoscopically, by passing the devices through the esophagus, preferably under endoscopic visualization. Alternatively, the devices may be implanted using surgical or laparoscopic procedures.

During implantation the pouch is secured at the gastroesophageal junction region G using sutures, clips, adhesives, stents or stent-like structures, or other suitable means. One suture attachment device found useful for applying sutures between the pouch and tissue is the "Sew-Right" suturing device available from LSI Solutions of Victor, N.Y. Although the pouch may be secured to the esophageal tissue, it is more preferable to apply sutures/clips below the Z-line to allow for attachment to the thicker tissue of the stomach wall.

Figure 1B:
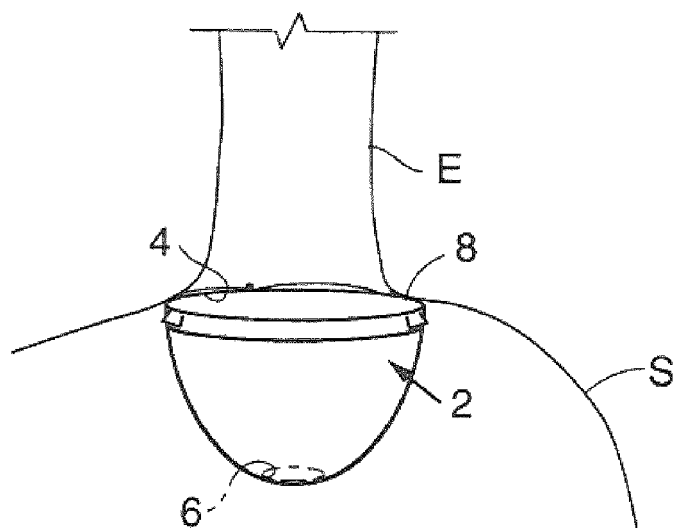
FIG. 1B is a perspective view of a satiation pouch provided without supplemental barrier features. The pouch is shown positioned in the stomach.
Figure 1C:
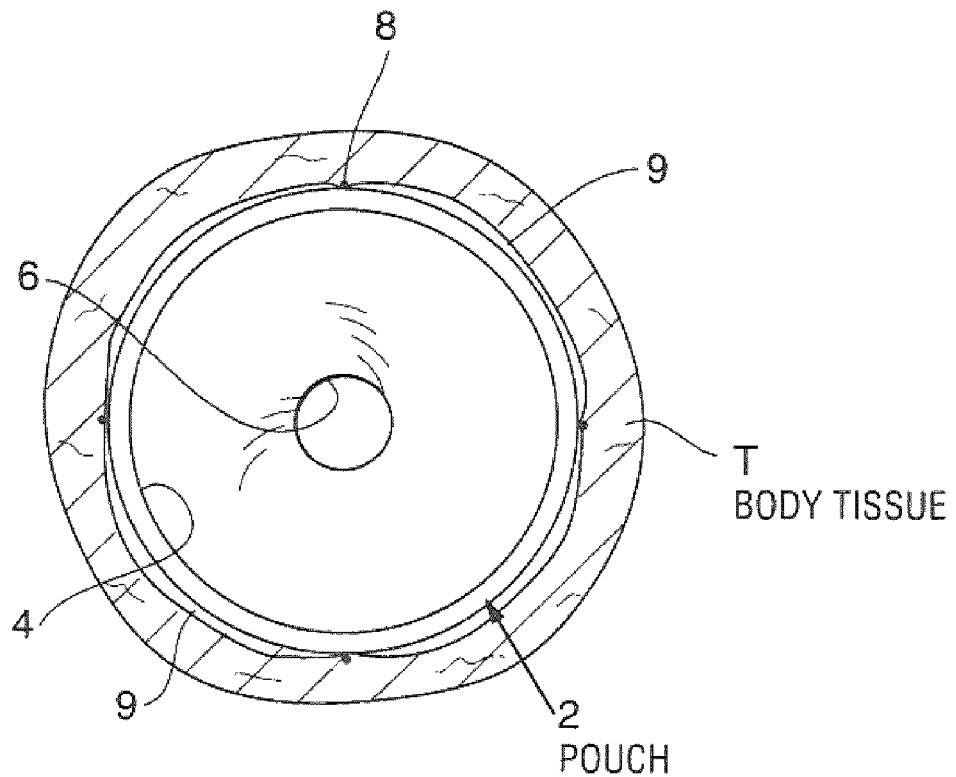
FIG. 1C is a top plan view of the satiation pouch of FIG. 1B shown within the stomach, and illustrating formation of gaps around the perimeter of the proximal opening.

Each of the described pouches includes a proximal opening and a distal exit port (see openings 4 and 6, respectively, of FIG. 1B). Because of its small volume (which may be on the order of approximately 2 cc-300 cc in volume, but is preferably in the range of 10-30 cc), the pouch functions to limit the amount of food that can be consumed at one time. Over time the food within this reservoir descends into the stomach through the exit port.

First Embodiment

Figure 2:
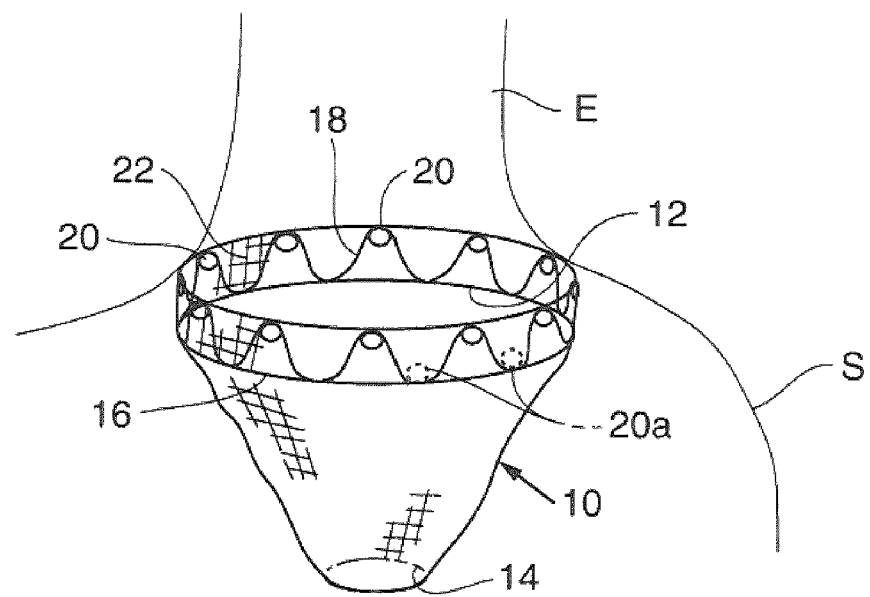
FIG. 2 is a perspective view of a first embodiment of a pouch having a circumferential barrier. The pouch is shown positioned in the stomach.
Figure 3:
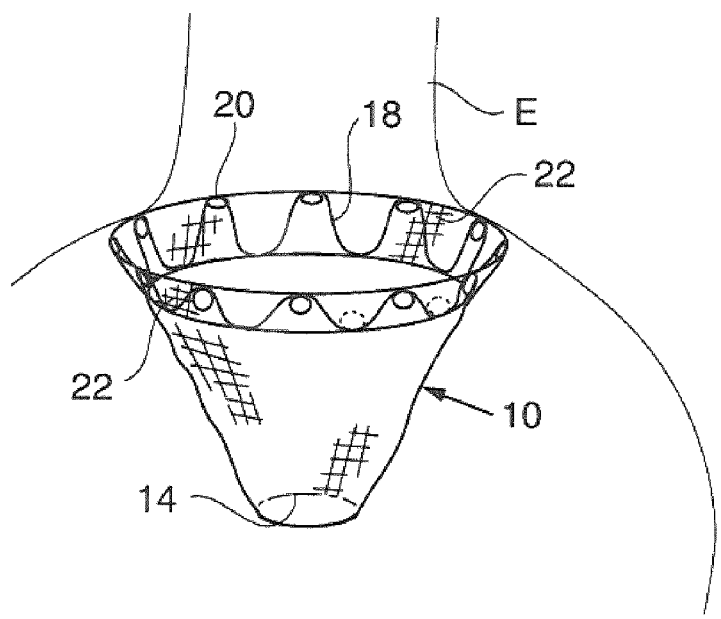
FIG. 3 is a perspective view similar to FIG. 2 showing expansion of the barrier into contact with tissue in a stomach having relatively broad proximal dimensions.

FIGS. 2 and 3 show a first embodiment of a pouch 10 having a proximal opening 12, distal exit port or opening 14 and a passage extending between the proximal and distal openings.

A resilient ring 16 surrounds the proximal opening 12 and a plurality of spring members 18 are attached to the ring 16. Spring members 18 are preferably biased in a radially outward direction and can pivot relative to ring 16. Although spring members 18 are preferably moveable independently of one another, they may take the form of multiple fingers formed along a single length of wire.

Anchor loops 20 are positioned on the spring members 18. The anchor loops 20 serve to receive sutures, clips or other attachment devices used to connect the pouch to surrounding tissue. The loops in each of the embodiments described in this application should be considered optional, since the pouch may alternatively be anchored directly to the tissue without the use of the loops 20.

The anchor loops 20 may be positioned in the outer apexes of the spring members as shown, and/or they may be positioned elsewhere such as closer to the ring 16. See, for example, loops 20a shown in dashed lines in FIG. 2. Ring 16, spring members 18 and loops 20 are preferably made of a resilient material (e.g. stainless steel, polymers etc.) suitable for use within the body.

Webbing 22 is connected to the spring members 18 along the circumference of the ring 16 to form a skirt-like member having a central opening. Webbing 22 is preferably formed of a flexible material that is substantially impermeable to masticated food. The material may be inelastic or elastic. Examples of suitable materials for the webbing 22 include those listed above for use with the pouch. When the pouch is secured within a patient, the webbing forms a barrier against passage of food between the pouch and surrounding tissue, and directs food into the proximal opening of the pouch. The webbing 22 and spring members 18 are preferably configured to form a dynamic seal with the surrounding tissue, so as to maintain a substantially consistent barrier despite stomach movement and flexure of the pouch. For example, the webbing 22 may be made expandable by using an elastic material and/or by including pleats in the webbing that allow for expansion. Also, the spring members 18 are preferably independently moveable and thus contribute to the dynamic nature of the barrier. In one variation on the first embodiment, the ring 16 and/or spring members 18 may be eliminated and the material of the webbing 22 itself may provide the necessary spring properties. In such an example, both the pouch and webbing, or the webbing along, may be formed of a resilient silicone or other resilient material.

During use, pouch 10 is introduced into the stomach S via the esophagus E and is held in the desired attachment location in the gastro-esophageal junction region. The pouch is anchored in place such as by connecting sutures or other attachment means to plurality of the anchor loops 20/20a or directly to the pouch and/or webbing to secure the pouch 10 in position. The outward radial forces of spring members 18 cause the spring members 18 to extend radially outwardly, carrying the webbing 22 into contact with the surrounding tissue, creating a barrier that minimizes passage of food around the pouch. If required by the anatomy of the patient's stomach, the spring members 18 will cause the webbing 22 to flare outwardly into contact with the surrounding tissue as shown in FIG. 3. Similarly, a narrower proximal stomach may restrict outward movement of the spring members 18 such that they angle the webbing in a slight inward direction.

Figure 4A:
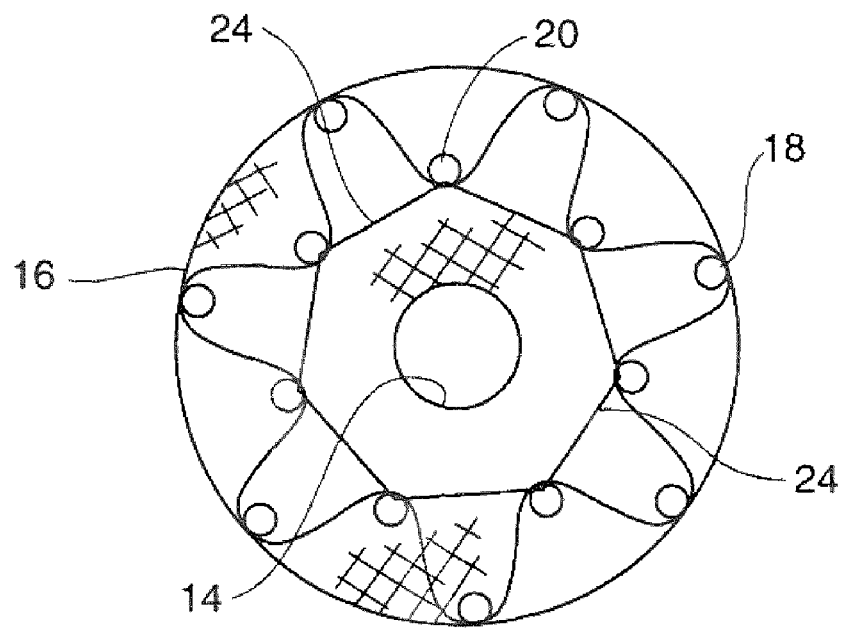
FIG. 4A is a top view of a pouch similar to the pouch of FIG. 2 showing the barrier and spring members restrained in a radially inward orientation.
Figure 4B:
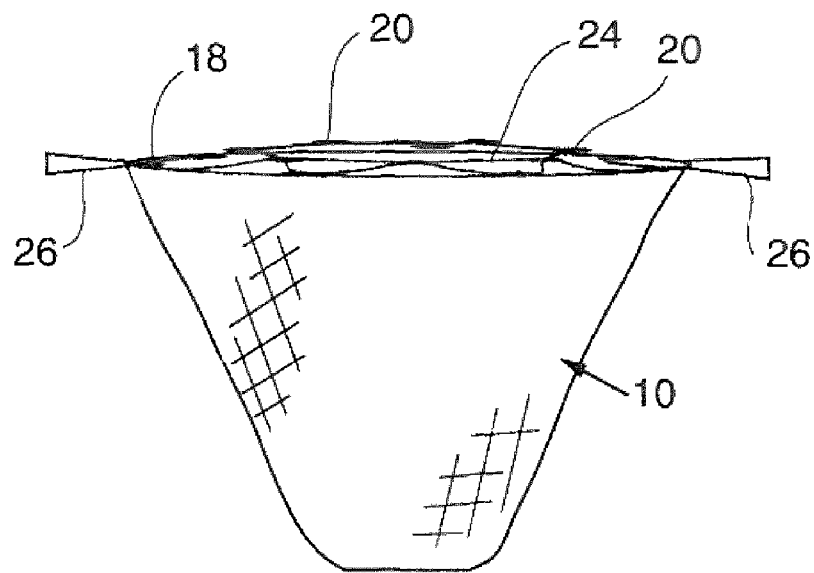
FIG. 4B is a side elevation view of the pouch of FIG. 4A.

If desired, the spring members 18 may be held in a laterally inward position as shown in FIGS. 4A and 4B during positioning of the pouch within the stomach. For example, temporary sutures 24 may be threaded through loops 20 and cinched to draw spring members 18 into the position shown in FIG. 4A. As illustrated in FIG. 4B, when drawn inwardly the spring members 18 and webbing 22 may have a relatively flat profile. The pouch may be anchored into position with the spring members 18 and pouch in the inward position, such as by attaching sutures to the loops 20 as described above, or by attaching sutures to additional anchor loops 26 that are separate from the spring members 18. Once the pouch has been sutured into place, temporary sutures 24 are snipped so as to release spring members 18, allowing the spring members 18 to carry the webbing into contact with the surrounding tissue.

Second Embodiment

Figure 5:
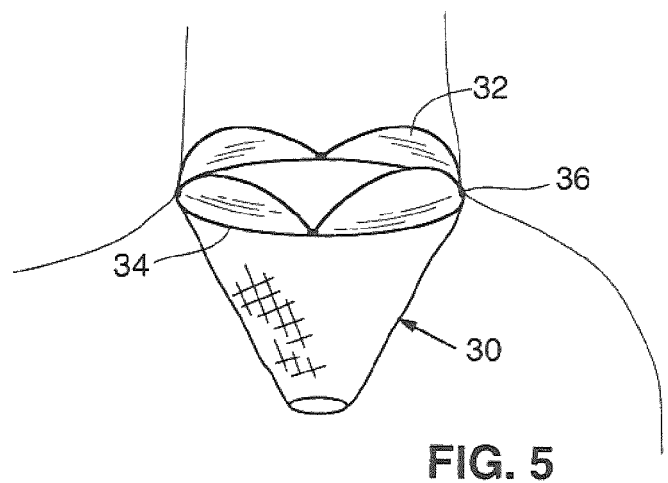
FIG. 5 is a perspective view similar to FIG. 2 showing a second embodiment having an alternative barrier configuration utilizing blade members.

A second embodiment of a pouch 30 is shown in FIG. 5. The second embodiment differs from the first embodiment primarily in that a plurality of blades 32 are mounted to resilient ring 34. Blades 32 may be formed of a variety of materials, including those listed above for forming the pouch. The blades are outwardly biased using wire reinforcements or other biasing structure. Anchors 36 are preferably positioned in spaced-apart locations between the blades 32. The pouch 30 is sutured in place by attaching sutures between anchors 36 and adjacent tissue. The blades 32 spring outwardly into contact with surrounding tissue, thereby creating a seal or barrier against passage of food that might otherwise pass between gaps forming between anchor points.

Third Embodiment

Figure 6:
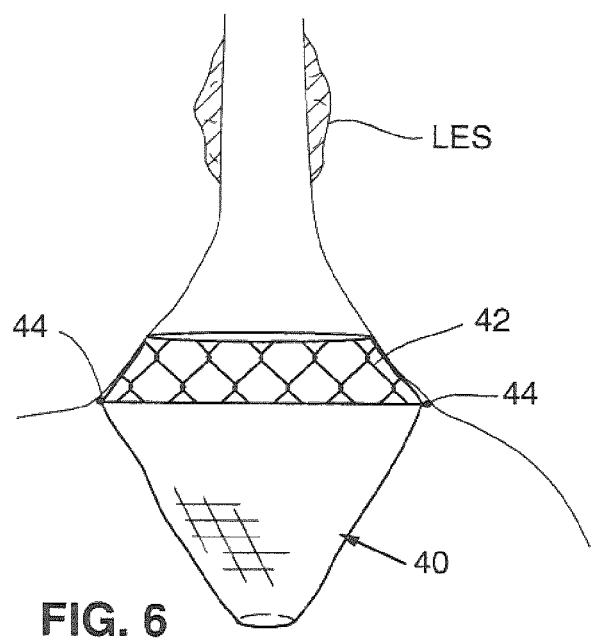
FIG. 6 is a perspective view similar to FIG. 2 showing a third embodiment having yet another barrier configuration utilizing a band of stent material.

FIG. 6 shows a third embodiment of a pouch 40, which uses an expandable stent-like band 42 for creating a seal or barrier. Band 42 is outwardly biased and may be formed of self-expanding material, such as stainless steel or a shape memory material such as nitinol or shape-memory polymer, and may be formed as a soft mesh or other framework formed of such materials in combination. The mesh may be created to have sufficiently small spaces between strands to form an effective barrier against a substantial portion of the ingested food, or it may be provided with a polymeric barrier that prevents ingested food from passing through the walls of the band 42. For example, the polymeric barrier may be a skin formed on the exterior or interior of the mesh, or the mesh may be encapsulated in polymeric material or the polymer may be disposed in the interstices of the mesh.

During use, the pouch 40 is secured in place by attaching sutures between anchors 44 and adjacent tissue of the gastro-esophageal junction region. Band 42 then expands into contact with the surround tissue to form the seal or barrier. The band 42 is preferably positioned beyond the lower esophageal sphincter (identified as LES in FIG. 6) to avoid interference with proper sphincter function.

Fourth Embodiment

Figure 7:
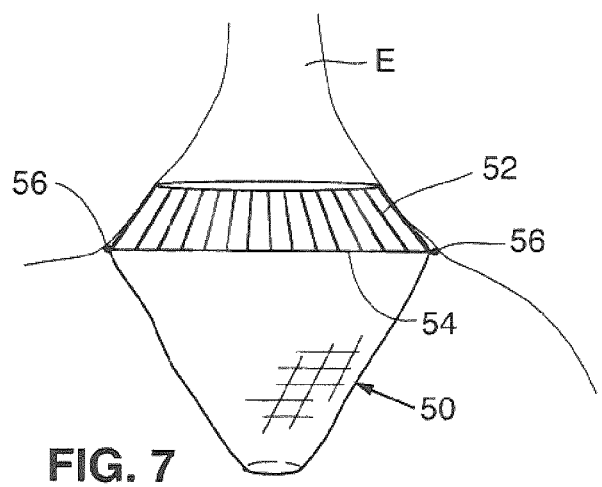
FIG. 7 is a perspective view similar to FIG. 2 showing a fourth embodiment having yet another barrier configuration utilizing leaf springs.

A fourth embodiment of a pouch 50, shown in FIG. 7, is similar to the previously described embodiments except that a plurality of leaf springs 52 are attached at the proximal end of the pouch. Springs 52 are outwardly biased to create the seal or barrier with surrounding tissue. As with prior embodiments, the pouch may include a resilient ring 54, and the pouch may be attached to surrounding tissue using sutures passed through anchors 56. In an alternative configuration, springs 52 may be coil springs which may be connected to a common structure at their proximal ends, or which may have free proximal ends.

Fifth Embodiment

Figure 8A:
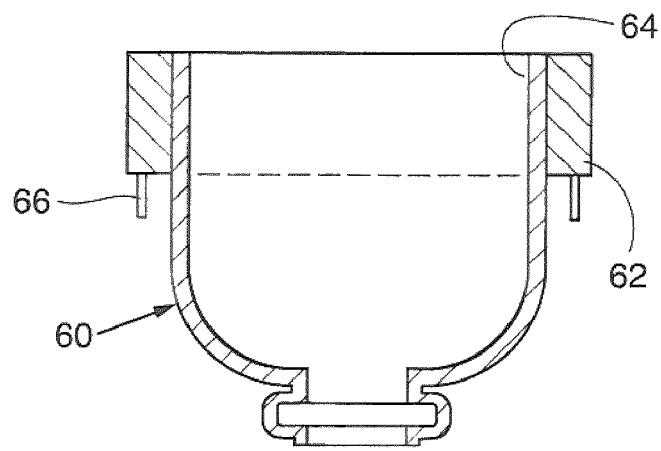
FIG. 8A is a cross-sectional side elevation view of a fifth embodiment of a pouch, which has a proximal rim that forms a circumferential seal with adjacent body tissue.
Figure 8B:
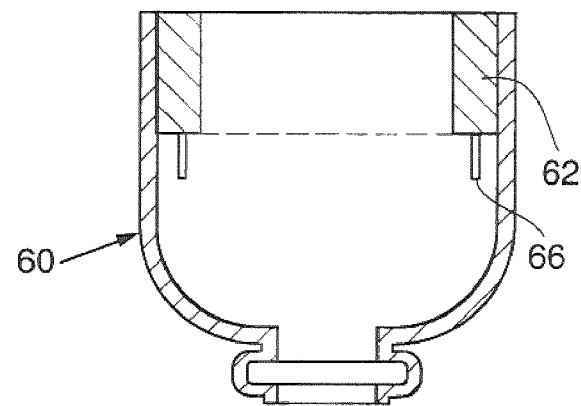
FIGS. 8B and 8C are cross-sectional side elevation views similar to FIG. 8A showing slight modifications to the rim position.
Figure 8C:
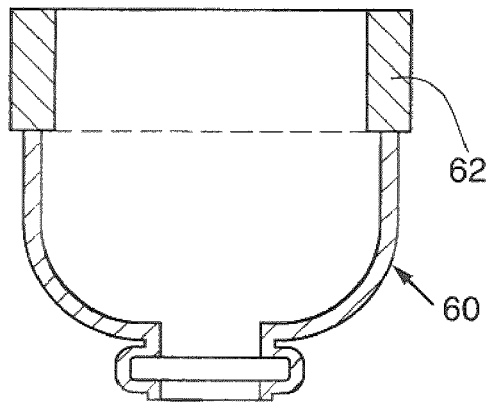
Figure 9A:
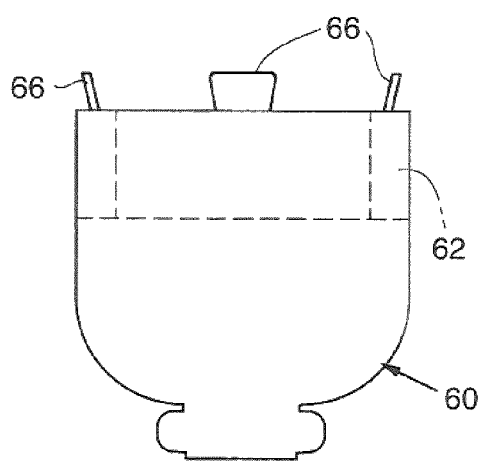
FIG. 9A is a side elevation view of the pouch of FIG. 8A, showing the rim in the inverted position.
Figure 9B:
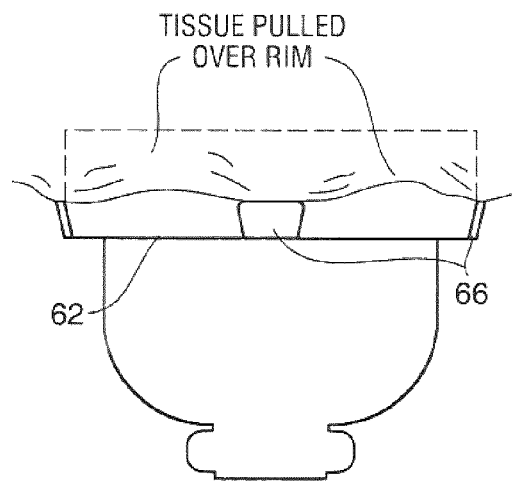
FIG. 9B is a side elevation view similar to FIG. 9B, showing the rim moved to the non-inverted position and drawing tissue over a portion of the rim.

Referring to FIG. 8A, a fifth embodiment of a pouch 60 includes an enlarged rim 62 surrounding the proximal opening 64 of the pouch 60. Rim 62 may extend slightly outwardly from the external surface of the pouch as shown in FIG. 8A, or slightly inwardly as shown in FIG. 8B, or both as shown in FIG. 8C. In one form of the fifth embodiment, anchor loops 66 extend from a distal portion of the rim 62 as shown in FIG. 8A. Before the pouch 60 is fixed within the body, the rim 62 is inverted inside the pouch 60 to the position shown in FIG. 9A. Once the rim has been inverted, anchor loops 66 extend in a proximal direction as shown. The pouch 60 is inserted into the stomach and the anchor loops 66 are secured to tissue using sutures or other attachment means. Next, the rim 62 is returned to the non-inverted position shown in FIG. 9B, causing the anchor loops 66 to return to the distally-oriented position. The loops 66 pull the attached tissue in a distal direction, around the edges of the rim 62, creating a taut and leak-resistant seal around the rim.

Figure 10A:
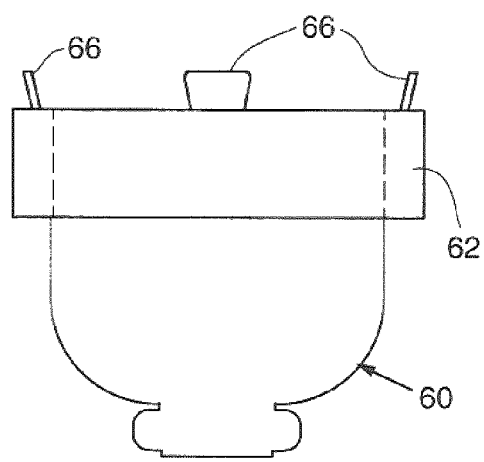
FIG. 10A is a side elevation view of an alternative to the pouch of FIG. 9A, showing the rim in an everted position.
Figure 10B:
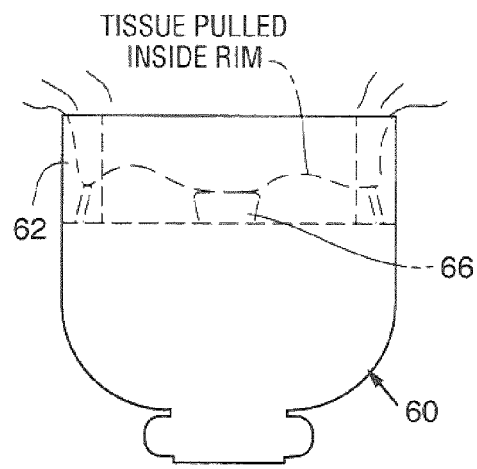
FIG. 10B is a side elevation view similar to FIG. 10B, showing the rim moved to the non-everted position and drawing tissue inside a portion of the rim.

In another form of the fifth embodiment, anchors 66 extend distally on an interior portion of the rim as shown in FIG. 8B. According to this form of the embodiment, before the pouch is fixed within the body, the rim 62 is everted outside the pouch 60 to the position shown in FIG. 10A—causing anchor loops 66 to extend in a proximal direction as shown. The pouch 60 is inserted into the stomach and the anchor loops 66 are secured to tissue using sutures or other attachment means. Next, the rim 62 is returned to the non-everted position shown in FIG. 10B, causing the anchor loops 66 to return to the distally-oriented position. The loops 66 pull the attached tissue in a distal direction, inside the edges of the rim 62, again creating a seal around the rim.

Sixth Through Eighth Embodiments

Figure 11:
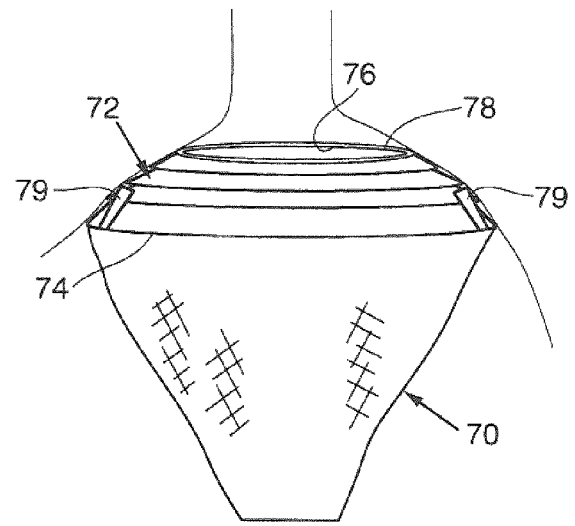
FIG. 11 is a schematic illustration showing a sixth embodiment of a pouch, which utilizes a bellows structure to create a barrier.

FIG. 11 shows a sixth embodiment of a pouch 70, which includes an expandable bellows structure 72, attached to a resilient ring 74. Bellows structure 72 includes a central channel 76 in alignment with the proximal opening (not shown) of the pouch 70, and is preferably formed of a flexible material that is substantially impervious to masticated food, and may be formed of materials similar to those listed for use in constructing the pouch. It may have a substantially cylindrical shape or a tapered geometry such as that shown in FIG. 11. At the proximal end of the bellows structure 72, surrounding the central channel 76, is a sealing ring 78 formed of a flexible material capable of forming a seal when urged into contact with body tissue.

Anchors 79 are attached to resilient ring 74 and are used to receive sutures, clips, etc that will connect the pouch to surrounding body tissue. Once the pouch has been fixed within the stomach, the bellows structure 72 expands the sealing ring 78 into contact with surrounding tissue, thereby creating a barrier or seal. As with prior embodiments, the resilience of the bellows allows the seal to be maintained despite movement of the stomach or expansion of the pouch.

Figure 12:
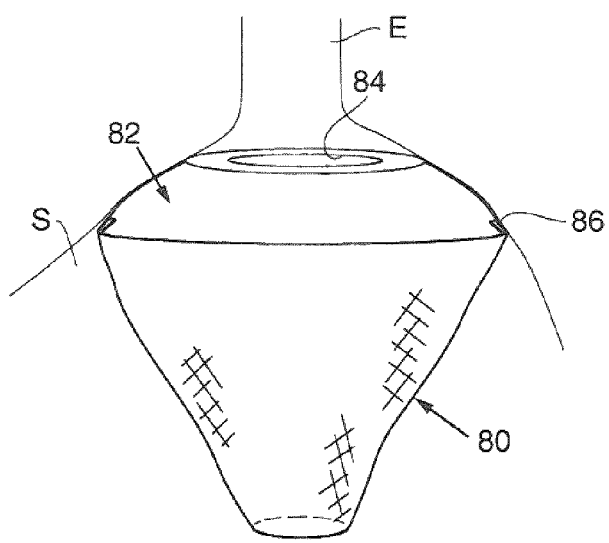
FIG. 12 is a schematic illustration showing a seventh embodiment of a pouch, which utilizes a conformable sealing ring.
Figure 13:
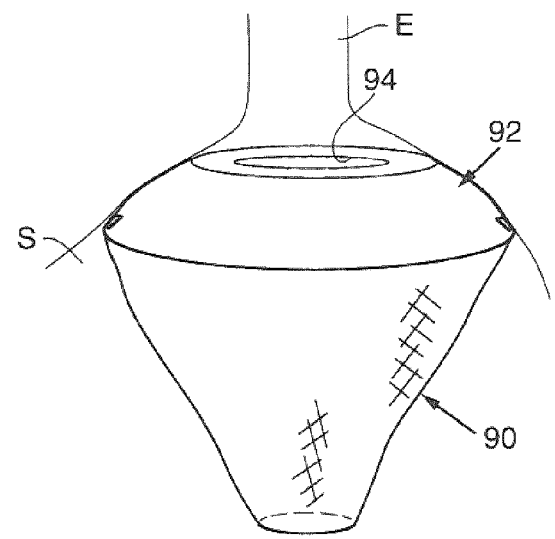
FIG. 13 is a schematic illustration showing an eighth embodiment of a pouch, which utilizes an inflatable sealing ring.

Similar embodiments are shown in FIGS. 12 and 13. In the seventh embodiment of FIG. 12, the proximal portion of the pouch 80 includes a conformable sealing ring 82 made of foam, sponge, silicone, or other conformable material that will seal against surrounding tissue when pressed into contact with the tissue. Ring 82 includes a central channel 84 and may include a cylindrical or tapered geometry. Anchors 86 receive sutures or clips used to fix the pouch to body tissue.

The eighth embodiment of FIG. 13 is a pouch 90 having a conformable sealing ring 92. Sealing ring 92 is formed of an elastic or inelastic bladder inflatable using an inflation fluid or gas. The bladder may be inflated prior to insertion into the stomach, or it may include a detachable inflation valve (not shown) that may be used to introduce inflation medium into the bladder after the pouch has been fixed within the stomach. As with the seventh embodiment, the sealing ring 92 may have a cylindrical or tapered geometry. Ingested food flows through a central channel 94 in the sealing ring 92 and into the pouch 90.

Ninth and Tenth Embodiments

Figure 14:
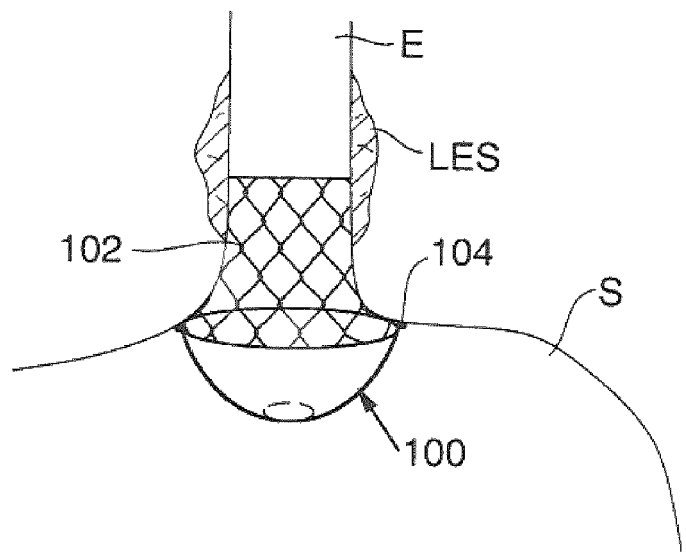
FIG. 14 is a schematic illustration showing a ninth embodiment of a pouch having an expandable barrier stent.
Figure 15:
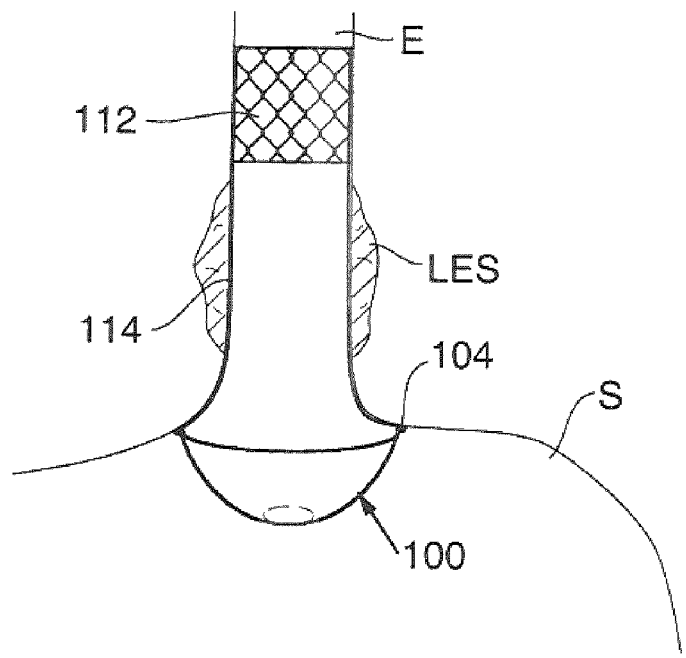
FIG. 15 is a schematic illustration shown a tenth embodiment of a pouch showing an alternative configuration of a barrier stent.

FIGS. 14 and 15 show ninth and tenth embodiments, respectively, of pouches having barrier devices for minimizing passage of food around, rather than through, the pouch. These embodiments are similar to the FIG. 6 embodiment in that they utilize a stent-like structure to expand against surrounding tissue to create the barrier or seal.

The barrier provided with the pouch 100 of FIG. 14 differs from that of FIG. 6 in that band 102 of stent material extends further into the esophagus, creating a seal with the tissue of the esophagus. This seal may be above, below, or within the lower esophageal sphincter (LES). As with each of the prior embodiments, anchors 104 receive sutures or clips that are used to fix the device to tissue in the region.

In the tenth embodiment shown in FIG. 15, a flexible tubular member 114 extends between the band 112 of stent material and the pouch 110. During use, member 114 may be positioned within the LES region while still preserving function of the LES.

Various embodiments of satiation devices have been described herein. These embodiments are given by way of example and are not intended to limit the scope of the present invention. It should be appreciated, moreover, that the various features of the embodiments that have been described may be combined in various ways to produce numerous additional embodiments. Also, while various materials, dimensions, shapes, implantation locations, etc. have been described for use with disclosed embodiments, others besides those disclosed may be utilized without exceeding the scope of the invention. Lastly, while the pouches have been described for use in controlling feelings of hunger, the barrier devices described herein may be equally suitable for use with other prosthetic devices positionable within the body, including prosthetic valves implanted in the lower esophagus or proximal stomach for controlling gastro-esophageal reflux disease (GERD).

We claim:

1. A method of treating obesity in a patient comprising:
    intraorally introducing into the patient's stomach a satiation device having a stent expandable within the esophagus, a stomach portion having a circumferential tissue-contact region, and a flexible member connecting the stent to the stomach portion;
    attaching the stomach portion to the patient's stomach, adjacent the gastro-esophageal junction,
    expanding the stent within the lower region of the patient's esophagus wherein the stomach portion of the device is positioned to contact tissue at its circumferential contact region to impart pressure against the wall of the patient's stomach adjacent the gastro-esophageal junction; and
    imparting pressure against portions of the body with the stomach portion to produce satiety in the patient.

2. The method of claim 1, wherein said attaching step includes attaching the device to the stomach by anchor loops positioned at a proximal end of the stomach portion.

3. The method of claim 1, wherein the stent includes a stent structure spring biased in a radially outward direction.

4. The method of claim 1, further comprising a plurality of anchors positioned on the stomach portion, and said attaching comprises passing a fastener through the anchor and into surrounding tissue.

5. The method of claim 1, wherein the portions of the body are selected from the stomach, esophagus, and esophageal sphincter.

6. The method of claim 1, wherein imparting pressure affects the levels of hormones to produce satiety.

7. The method of claim 1, wherein the stomach portion is formed of a flexible material.

8. The method of clam 7, wherein the flexible material is reinforced with supporting members.

\* \* \* \* \*